United States Patent
Sadayama

(10) Patent No.: US 6,685,847 B2
(45) Date of Patent: Feb. 3, 2004

(54) METHOD FOR OBSERVING CROSS-SECTIONAL STRUCTURE OF SAMPLE

(75) Inventor: Shoji Sadayama, Chiba (JP)

(73) Assignee: Seiko Instruments Inc., Chiba (JP)

( * ) Notice: Subject to any disclaimer, the term of this patent is extended or adjusted under 35 U.S.C. 154(b) by 135 days.

(21) Appl. No.: 09/754,645

(22) Filed: Jan. 4, 2001

(65) Prior Publication Data

US 2001/0010841 A1 Aug. 2, 2001

(30) Foreign Application Priority Data

Jan. 14, 2000 (JP) .......................... 2000-010159

(51) Int. Cl.$^7$ .............................................. G01N 13/00

(52) U.S. Cl. ........................... 216/37; 216/39; 250/306; 250/307; 264/406; 427/8; 438/695; 438/702

(58) Field of Search ................... 216/37, 39; 250/306, 250/307, 309; 264/406; 427/8; 438/695, 702

(56) References Cited

U.S. PATENT DOCUMENTS

| 5,451,529 A | * | 9/1995 | Hsu et al. ...................... 438/18 |
| 6,136,707 A | * | 10/2000 | Cohen ......................... 438/687 |
| 6,177,149 B1 | * | 1/2001 | Tada et al. ................... 427/576 |
| 6,194,720 B1 | * | 2/2001 | Li et al. ...................... 250/311 |

FOREIGN PATENT DOCUMENTS

JP        11307417 A  * 11/1999   ......... H01L/21/027

* cited by examiner

Primary Examiner—Allan Olsen
(74) Attorney, Agent, or Firm—Adams & Wilks

(57) ABSTRACT

A cross-section is obtained in which a sample shape is clearly delineated by forming a covering layer of a material different from that of the sample surface on the sample surface, forming a protective layer on the covering layer forming a hole in the protective and covering layers and the sample surface to expose the cross-section, and tilting the sample and scanning the cross-section with a focused ion beam so as to obtain a microscopic image of the cross-section. By forming the covering layer of a material different from that of the sample surface, the shape of the sample can be clearly viewed in the obtained image.

18 Claims, 3 Drawing Sheets

Before Etching

After Rough Etching

After Fine Etching

METHOD FOR OBSERVING CROSS-SECTIONAL STRUCTURE OF SAMPLE

BACKGROUND OF THE INVENTION

The present invention relates to a method for observing the cross-sectional shape of a sample surface using a focussed ion beam apparatus, and more particularly relates to cross-sectional processing applied to observing grooves occurring with semiconductor elements and thin-film magnetic heads, etc.

Focussed ion beam apparatus are capable of processing and microscopically observing materials and in recent years have often been used in the processing and observation of the cross-section of samples, down to cross-sectional sizes for the most part from a few μm to a few tens of μm. In a basic procedure shown in FIG. 3A, first, locations of the sample which it is wished to subject to cross-sectional observation are specified (portions surrounded by a dashed line). However, it is necessary to open up the exposed part of the cross-section towards the front in order to monitor the cross-section. It is necessary to perform beam scanning from a severe angle with respect to the cross-section in order to obtain a microscopic image of the cross-section. When the processing regions are specified, the surface of the sample is subjected to rough processing using an ion beam from a vertical direction as shown in FIG. 3B. This processing is to open up a hole required for observation by causing the cross-section to be monitored to be exposed and therefore employs a large current beam to perform rough etching. This means that damage is incurred by the cross-section to be observed, as shown in FIG. 3B. When the hole-opening process finishes, polishing of the cross-section to be observed is carried out by etching with the beam current lowered, so as to expose the clean cross-section shown in FIG. 3C. A supporting table is then tilted and beam scanning is performed by irradiation with an ion beam from a severe angle with respect to the cross-section, and a scanning ion microscope image is obtained for the cross-section it is wished to observe.

However, an operation is carried out in advance to form a protective film on the material surface in order to prevent damage by the focused ion beam during processing. This operation is referred to as deposition. Typically, a protective layer is formed by spraying $W(CO)_6$ or phenanthrene etc. onto the processing portions from a gas gun. However, when the material for the protective layer is the same as the material of the substance for the surface of the sample, a boundary of the original sample surface and the protective layer cannot be distinguished in an observed microscopic image. In particular, when the cross-sectional image to be observed is the surface shape of a groove, large amounts of protective film material are deposited at the groove so that the groove becomes buried and the original groove shape cannot be distinguished in a microscopic image.

In order to resolve the aforementioned problems with regards to technology for processing and observing cross-sections using a focused ion beam, the present invention sets out to provide a method for obtaining a microscopic image where the shape of an original material surface is clearly regardless of protective layer forming material becoming deposited at the surface of a sample when processing the cross-section.

SUMMARY OF THE INVENTION

The present invention achieves this object by first forming a covering layer of a different material to the material of a sample surface at the surface of the as-yet unprocessed sample. A protective layer is then formed by deposition and this portion is subjected to cross-section processing. A covering layer of a different material there exists at the boundary of the original sample surface and the protective layer deposited by deposition. The presence of the covering layer of a different substance in a microscopic image then enables the shape of the original sample surface to be clearly depicted.

DETAILED DESCRIPTION OF THE PREFERRED EMBODIMENT

A characteristic of the present invention is that a covering layer of material different to the material of the sample surface is formed at the sample surface prior to forming a protective layer at a processing portion of the sample.

Theoretically speaking, a covering layer of a material different to the substance forming the sample surface is formed at the surface of the sample which is as yet un-processed, with it being preferable for the sample to be left in a state that enables identification after cross-sectional processing. However, in this embodiment a method is selected where an appropriate material is affixed by sputtering or vapor deposition, with irradiation of an ion beam then taking place using a gas gun.

Further, this operation is carried out using a focused ion beam apparatus. It is therefore also possible to form a covering layer in a straightforward manner by opening a hole by irradiating an appropriate region of the sample isolated from the cross-section of the sample to be monitored using irradiation with a focused ion beam, and spraying on a substance different to the surface material such as a metallic material such as iron or nickel other than carbon when, for example, the surface is a resist, so as to cause reattachment to the sample surface.

When a hole is opened when the surface material is the same as the material of the portion to be observed, first, the same material is sprayed on. The affixing of the sprayed on material differs from the case of deposition forming the protective layer not just in that a large layer is affixed but also in that the covering layer is gradually affixed to the surface so that the surface shape cannot be distinguished.

Further, in the case of the same type of material also, a compound made with a substance (Ga etc.) that can be used with an ion beam is mixed and affixed and surface shape can therefore be maintained in a sufficient manner.

FIG. 1 shows the processing procedure of the present invention.

Figure 1A:
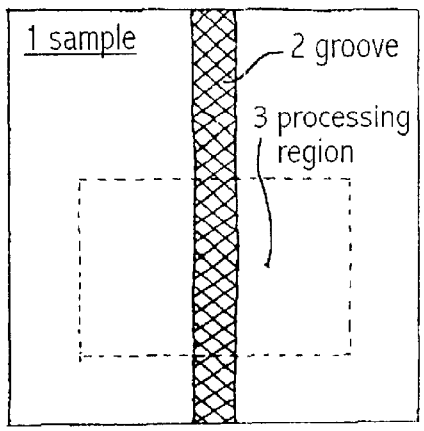
FIG. 1A is a view illustrating a procedure for processing a cross-section to be observed and a method of taking an observed microscopic image.

In FIG. 1A, a processing region 3 including a groove 2 it is wished to observe within a sample 1 is specified, and a covering layer is formed on the sample surface using an appropriate method described above.

Figure 1B:
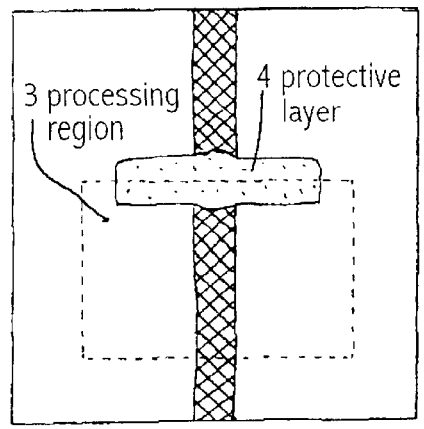
FIG. 1B is a view illustrating a procedure for processing a cross-section to be observed and a method of taking an observed microscopic image.
Figure 1C:
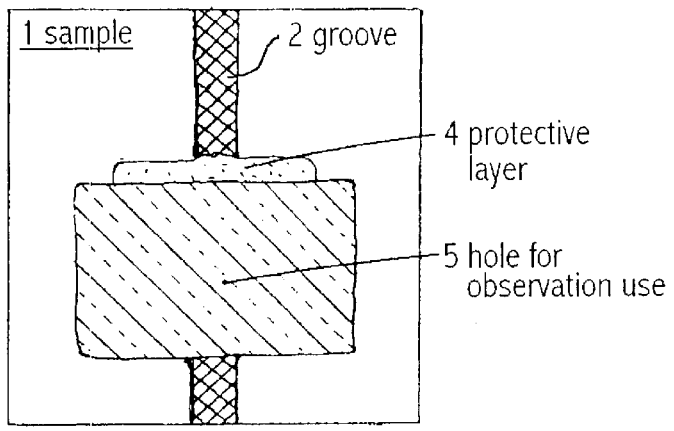
FIG. 1C is a view illustrating a procedure for processing a cross-section to be observed and a method of taking an observed microscopic image.
Figure 3:
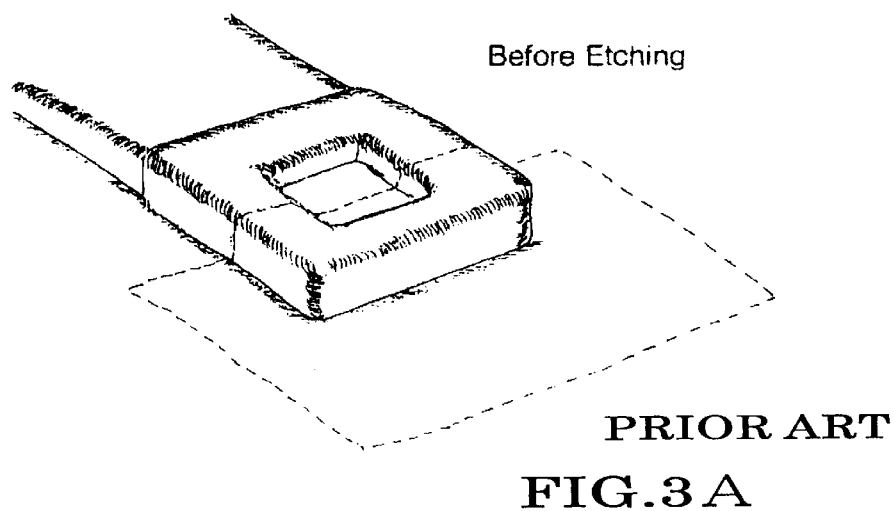
FIG. 3A is a view illustrating a related procedure for processing a cross-section of a sample to be observed.
FIG. 3B is a view illustrating a related procedure for processing a cross-section of a sample to be observed.
FIG. 3C is a view illustrating a related procedure for processing a cross-section of a sample to be observed.
Figure 3:
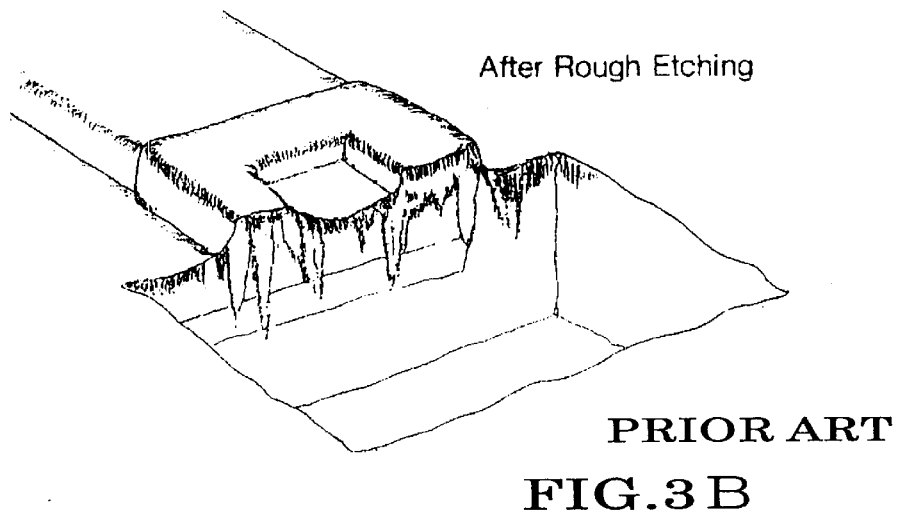
Figure 3:
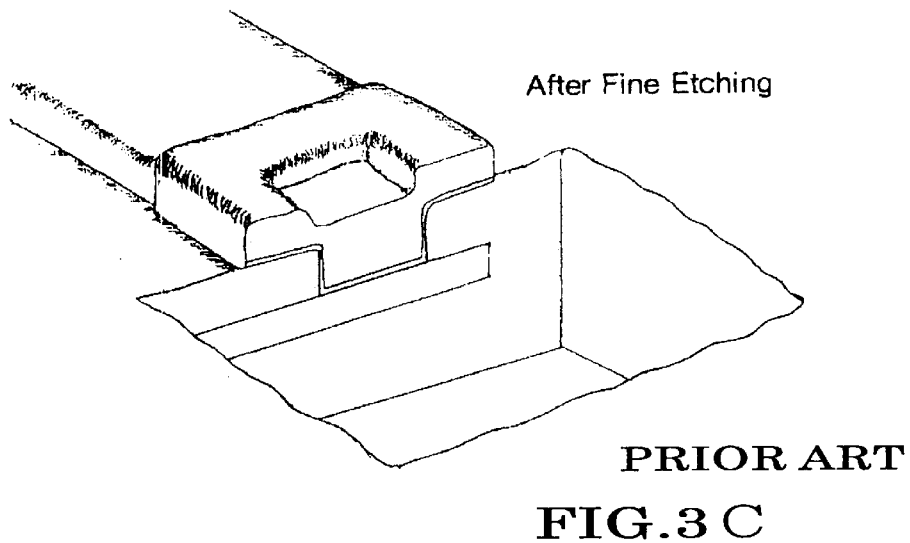

In FIG. 1B, a prescribed gas is sprayed from a gas gun in the observed cross-section at the stage of forming a covering layer, irradiation with an ion beam is carried out and a protective layer 4 is formed. The cross-section to be monitored is then processed in the same manner as in the related art shown in FIG. 3 with the protective layer 4 formed. However, a hole 5 for observation use is opened up by rough etching as shown in FIG. 1C, the beam current is dropped when the hole reaches the required size, and the cross-section to be observed is polished.

The supporting table is then tilted with a cross-section to be observed 6 in a cleanly polished state, ion beam scanning is performed at a severe angle (approximately sixty degrees) with respect to the cross-section to be observed 6 and a microscopic image of the cross-section to be observed 6 is obtained.

Figure 1D:
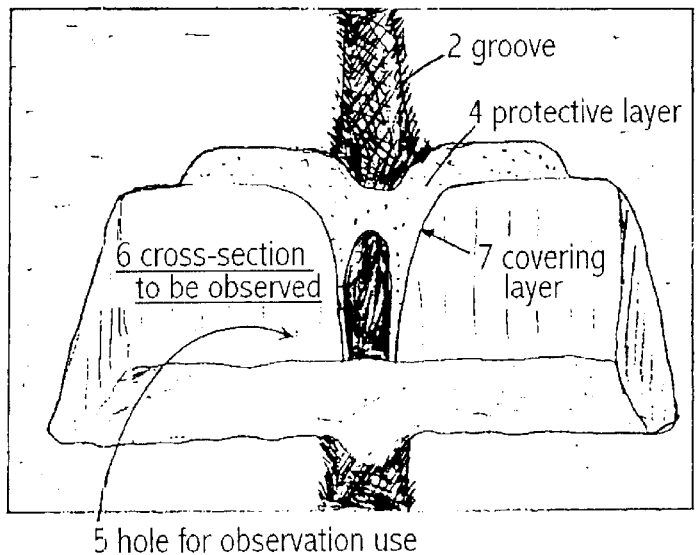
FIG. 1D is a view illustrating a procedure for processing a cross-section to be observed and a method of taking an observed microscopic image.

FIG. 1D is a perspective view of the processing section from the direction of irradiation of the scanning beam. As shown in FIG. 1D, material of the protective layer 4 deposited onto the surface of the groove 2 becomes affixed down to a deep position, and a bridge shape spans the vicinity of a shallow inlet. However, the shape of the original surface cross-section of the groove 2 it is wished to observe is maintained by the existence of a covering layer 7.

Therefore, even if the material of the sample surface and the material of the protective layer are of the same type, if a scanning ion microscopic image of the cross-section to be observed 6 is taken, the shape of the surface of the original cross-section is clearly depicted by the covering layer 7 that is a boundary line.

The method of the present invention is effective in the case of samples where the surface of a magnetic head or semiconductor element etc. is covered with a resist or for samples adopting carbon polymer as a material when deposition is performed using carbon, and is also effective in the case of samples where the uppermost surface of a semiconductor element for a via contact forming process stage is covered in tungsten.

Embodiment 1

Figure 2:
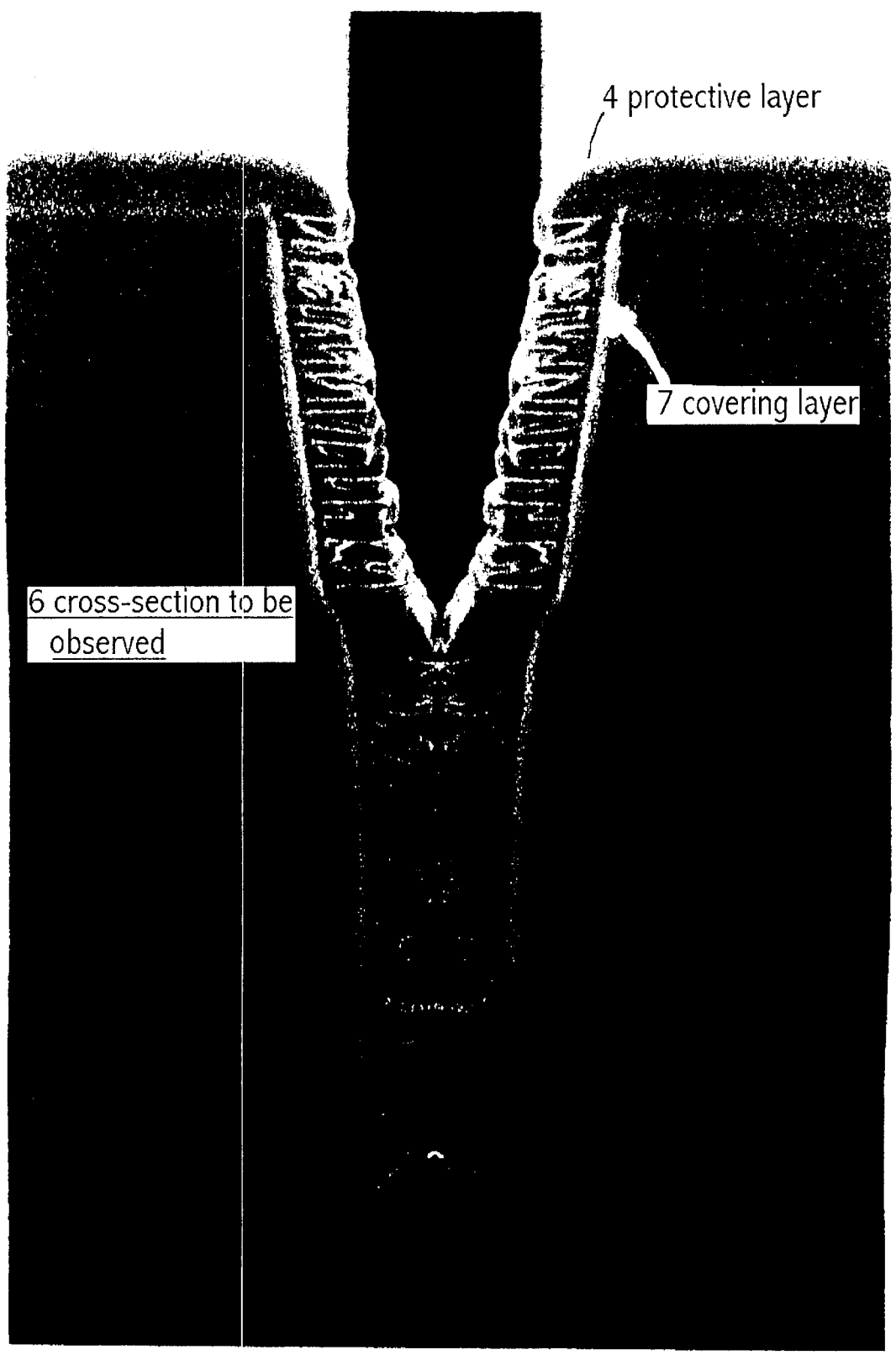
FIG. 2 is a cross-sectional microscopic image of a groove of a thin-film magnetic head processed by the procedure of the present invention.

A scanning ion microscopic image of a cross-section to be observed processed by the procedure of the present invention taking a thin-film magnetic head as a sample is shown in FIG. 2.

In this embodiment, in order to form the covering layer 7 at the a sample surface, a method is adopted where a region other than the portion to be observed is irradiated with a focused ion beam so that material different from the surface material is caused to become reaffixed to the sample surface in the portion to be observed. A benefit of this method is that it is not necessary to perform specific pre-processing when forming the covering layer which enables implementation within the focused ion beam apparatus.

A hole in the region of 5 $\mu$m by 5 $\mu$m is opened in the sample, with the processed surface being monitored until the substrate appears. By blowing all of the sample on to the substrate, material differing from the surface substance can be reliably blown on.

It is only necessary to implement this operation to the extent that the film adhered so as to cover the surface of the sample enables identification of the cross-section image. This extent will differ depending on the material and if the material is well known, it may also be possible to implement part of a series of processing steps using software.

At the stage where the covering layer 7 of an appropriate thickness is formed, irradiation with a focused ion beam takes place while blowing phenanthrene onto the vicinity of the cross-section to be observed using a gas gun so that the protective layer 4 of carbon is formed.

At this stage, processing of the cross-section is entered, and processing to open the hole 5 for observation is performed using a beam current of 4 nA. With this type of rough etching processing, a beam current typically in the region of 2 to 5 nA is employed. The main point of this is to open a hole in a rapid manner so that the cross-section to be monitored is damaged. The high processing speed achieves etching of the material at 0.5 to 1 $\mu$m$^3$/sec. The damaged cross-section to be observed 6 is then polished by fine etching, but this is implemented at a beam current of 400 pA. This etching is performed in order to cleanly polish the cross-section to be monitored that has incurred the damage and the beam current is therefore kept low, with the etching performed at a speed of 0.1 $\mu$m$^3$/sec. The supporting table is then tilted with the cross-section to be observed 6 in a polished state, and irradiation of an ion beam is performed at an angle of approximately 60 degrees with respect to the cross-section to be observed 6. This then gives the raster-type scanned scanning ion microscopic image shown in FIG. 2.

As can be discerned from observing the microscopic image, the original channel surface shape of the magnetic head is clearly depicted at the cross-section to be observed 6 by the covering layer 7 as a boundary line with the protective layer 4 deposited on the sample surface.

In the present invention, a covering layer of a material different to the material of the sample surface is formed on the original sample surface prior to executing processing. After this, deposition of the protective layer and processing of the cross-section to be monitored is performed. The shape of the original sample surface is therefore maintained by the presence of the covering layer and can be clearly observed in the cross-sectional image even when the material of the protective layer formed on, for example, the sample surface is the same as the material of the sample surface.

Further, observation is carried out using focused ion beam apparatus. Troublesome operations such as pre-processing for forming of the covering layer in another apparatus therefore do not have to take place, a hole is opened up in the sample by irradiating the vicinity of the part of the sample to be observed with a focussed ion beam, and material other than the surface substance can be dispersed by etching.

What is claimed is:

1. A method of observing a cross-sectional structure of a sample, comprising the steps of:

forming a covering layer of a material different from a substance of the sample surface on the sample surface in a region at which the cross-sectional structure is to be observed;

forming a protective layer on the covering layer by spraying a gas towards the covering layer using a gas gun while irradiating the covering layer with a focused ion beam;

irradiating the protective layer with a high-current focused ion beam to form a hole exposing a cross-section to be observed;

irradiating the cross-section with a low current ion beam so as to polish the cross-section; and tilting the sample and scanning the cross-section to be observed with a focused ion beam so as to obtain a microscopic image of the cross-section.

2. A method of observing a cross-sectional structure of a sample according claim 1; wherein the step of forming the covering layer comprises the step of etching a region of the sample spaced apart from the cross-section area so that etched substances become reattached to the region of the cross-section to be observed.

3. A method of observing a cross-sectional structure of a sample according to claim 1; wherein the step of forming the covering layer is performed by deposition using a gas gun for spraying a gas towards the sample surface while performing irradiation of the sample surface with an ion beam.

4. A method of observing the cross-sectional structure of a sample according to claim 1; wherein the step of forming the covering layer is performed by sputtering.

5. A method of observing the cross-sectional structure of a sample according to claim 1; wherein the step of forming the covering layer is performed by vapor deposition.

6. A method of obtaining a cross-section of a sample, comprising the steps of:

using a focused ion beam to deposit a covering layer on a surface of the sample in a region at which the cross-section is to be obtained, the covering layer being formed of a material different from that of the sample surface;

using the focused ion beam to deposit a protective layer over the covering layer;

using the focused ion beam to form a hole in the sample surface to obtain the cross-section; and observing the cross-section by tilting the sample after forming the hole and scanning the cross-section with the focused ion beam so as to obtain a microscopic image of the cross-section.

7. A method of obtaining a cross-section of a sample according to claim 6; wherein the step of depositing a covering layer is performed by etching the sample in a region apart from the region where the cross-section is to be obtained to deposit etched materials onto the region where the cross-section is to be obtained.

8. A method of obtaining a cross-section of a sample according to claim 6; wherein the step of depositing a covering layer is performed by sputtering.

9. A method of obtaining a cross-section of a sample according to claim 6; wherein the step of depositing a covering layer is performed by vapor deposition.

10. A method of obtaining a cross-section of a sample according to claim 6; wherein the step of forming the covering layer comprises the steps of spraying a gas towards the sample surface using a gas gun while irradiating the sample surface with an ion beam.

11. A method of obtaining a cross-section of a sample according to claim 6; wherein the step of depositing a protective layer over the covering layer is performed by vapor deposition.

12. A method of obtaining a cross-section of a sample according to claim 6; wherein the step of depositing a protective layer over the covering layer comprises the steps of spraying a gas towards the sample surface using a gas gun while irradiating the sample surface with an ion beam.

13. A method of obtaining a cross-section of a sample according to claim 6; wherein the step of forming a hole in the sample surface comprises the step of irradiating the protective layer with a high-current focused ion beam to form the hole exposing the cross-section.

14. A method of obtaining a cross-section of a sample according to claim 6; further comprising the step of polishing the cross-section after forming the hole.

15. A method of obtaining a cross-section of a sample according to claim 14; wherein the step of polishing the cross-section comprises the step of irradiating the cross-section with a low current ion beam.

16. A method of obtaining a cross-section of a sample according to claim 6; further comprising the step of observing the cross-section.

17. A method of obtaining a cross-section of a sample according to claim 16; wherein the step of observing the cross-section comprises the steps of tilting the sample and scanning the cross-section with a focused ion beam so as to obtain a microscopic image of the cross-section.

18. A method of obtaining a cross-section of a sample according to claim 6; further comprising the step of polishing the cross-section using the focused ion beam after forming the hole.

* * * * *